United States Patent [19]

Chu et al.

[11] Patent Number: 5,190,926

[45] Date of Patent: * Mar. 2, 1993

[54] 3'-AZIDO-2',3'-DIDEOXYPYRIMIDINES AND RELATED COMPOUNDS AS ANTIVIRAL AGENTS

[75] Inventors: Chung K. Chu, Athens; Raymond F. Schinazi, Tucker, both of Ga.

[73] Assignees: University of Georgia Research Foundation, Inc., Athens; Emory University, Atlanta, both of Ga.

[*] Notice: The portion of the term of this patent subsequent to Apr. 10, 2007 has been disclaimed.

[21] Appl. No.: 434,521

[22] Filed: Nov. 6, 1989

Related U.S. Application Data

[63] Continuation of Ser. No. 104,438, Oct. 2, 1987, Pat. No. 4,916,122, which is a continuation-in-part of Ser. No. 7,473, Jan. 28, 1987, abandoned.

[51] Int. Cl.$^5$ .............................................. A61K 31/70
[52] U.S. Cl. .................................. 514/49; 536/26.21; 536/26.26.26.8; 514/50; 514/51
[58] Field of Search ...................... 514/49, 50, 51, 885; 536/23

[56] References Cited

U.S. PATENT DOCUMENTS

| | | | |
|---|---|---|---|
| 3,282,921 | 11/1966 | Verheyden et al. | 514/49 |
| 3,687,931 | 8/1972 | Verheyden et al. | 536/23 |
| 3,755,295 | 8/1973 | Verheyden et al. | 536/23 |
| 3,775,397 | 11/1973 | Etzold et al. | 536/23 |
| 3,817,982 | 6/1974 | Verheyden et al. | 536/23 |
| 4,071,680 | 1/1978 | Cook | 536/23 |

(List continued on next page.)

FOREIGN PATENT DOCUMENTS

| | | |
|---|---|---|
| 0196185 | 10/1986 | European Pat. Off. |
| 0196185 | 10/1986 | European Pat. Off. |
| 0199451 | 10/1986 | European Pat. Off. |
| 0217580 | 4/1987 | European Pat. Off. |
| 0217580 | 4/1987 | European Pat. Off. |
| 3608606 | 9/1986 | Fed. Rep. of Germany |
| 224490 | 7/1985 | German Democratic Rep. |

(List continued on next page.)

OTHER PUBLICATIONS

De Clercq, et al., *Pharm.* 97, 174446t (1982).
Busson, et al., *Chem. Abstracts* 96, 69346s (1982).
Nth. App. 81 00, 177 *Chem. Abstracts* 98, 4753u (1983).
Krenitsky, et al. *J. Med. Chem.* 26(6) 891–895 (1983).
Lin et al., *J. Med. Chem.* 26, 544–548 (1983).
Lin, et al., *J. Med. Chem.* 26, 1691–1696 (1983).

(List continued on next page.)

*Primary Examiner*—Ronald W. Griffin
*Attorney, Agent, or Firm*—Kilpatrick & Cody

[57] ABSTRACT

A pharmaceutical composition in dosage unit form comprising a therapeutically effective HIV inhibitory amount of a compound having the formula:

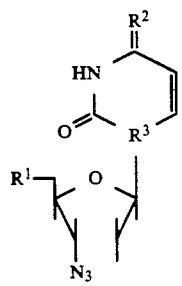

wherein $R^1$ is selected from the group consisting of OH, $C_{1-4}$ acyl, sulfate phosphate, and amino; $R^2$ is O or NH, and $R^3$ C or N, or a pharmacologically acceptable acid addition salt thereof, in association with a pharmaceutical carrier.

3 Claims, 4 Drawing Sheets

U.S. PATENT DOCUMENTS

| | | | |
|---|---|---|---|
| 4,093,715 | 6/1978 | Lin et al. | 514/49 |
| 4,128,639 | 12/1978 | Lin et al. | 536/23 |
| 4,210,638 | 7/1980 | Greer | 536/23 |
| 4,230,698 | 10/1980 | Bobek et al. | 536/23 |
| 4,331,662 | 5/1982 | Eckstein et al. | 514/49 |
| 4,604,382 | 4/1986 | Lin et al. | 514/49 |
| 4,710,492 | 12/1987 | Lin et al. | 514/50 |
| 4,724,232 | 2/1988 | Rideout et al. | 514/50 |
| 4,916,122 | 4/1990 | Chu et al. | 514/50 |

FOREIGN PATENT DOCUMENTS

| | | |
|---|---|---|
| 8506868 | 3/1986 | United Kingdom . |
| 8506869 | 4/1986 | United Kingdom . |
| 8511774 | 4/1986 | United Kingdom . |
| 8511775 | 4/1986 | United Kingdom . |
| 8523881 | 4/1986 | United Kingdom . |
| 8523878 | 9/1986 | United Kingdom . |
| 8603447 | 9/1986 | United Kingdom . |
| 8603450 | 9/1986 | United Kingdom . |
| 8608272 | 9/1986 | United Kingdom . |
| 8615322 | 9/1986 | United Kingdom . |
| 8603719 | 10/1986 | United Kingdom . |

OTHER PUBLICATIONS

Laitseva, et al. Carbohydrates 101, 192378c (1984).

Fox, et al., Herpes Viruses and Virus Chemotherapy Elsevier Science Publishers B.V. (Biomedical Division) 53–56 (1985).

Colla, et al., *Eur. J. Med. Chem.—Chim. Ther.* 20(4) 295–301 (1985).

Schinazi, et al., *Antimicrobial Agents and Chemotherapy* 28(4), 552–560 (1985).

Brubaker, et al., *Chem. Abstracts* 102: 226110x (1985).

3'-AZIDO-2',3'-DIDEOXYPYRIMIDINES AND RELATED COMPOUNDS AS ANTIVIRAL AGENTS

The U.S. Government has rights in this invention as a result of the investigations leading to this invention being funded in part by a VA Merit Review Award.

This application is a continuation of U.S. Ser. No. 07/104,438, filed Oct. 2, 1987, issued as U.S. Pat. No. 4,916,122, Apr. 10, 1990, which is a continuation-in-part of U.S. Ser. No. 07/007,473, filed Jan. 28, 1987, now abandoned.

BACKGROUND OF THE INVENTION

1. Field of the Invention

The present invention relates to 3'-azido-2',3'-dideoxyuridine (referred to as CS-87 herein) and 3'-azido-2',3'-dideoxycytidine (referred to as DDC herein) and structurally related compounds as agents for prevention and treatment of viral diseases, particularly human immunodeficiency virus (HIV; also known as HTLV-III/LAV), which causes acquired immunodeficiency syndrome (AIDS). The invention is particularly directed to compositions containing 3'-azido-2',3'-dideoxyuridine or 3'-azido-2',3'-dideoxycytidine and to a method of treatment of AIDS which involves treating the person afflicted with this disease with a composition including one of the compounds of the present invention.

2. Brief Description of the Background

AIDS was recognized as early as 1979. The number of cases reported to the Centers for Disease Control (CDC) has increased dramatically each year since then, and in 1982 the CDC declared AIDS a new epidemic. There are now approximately 30,000 reported cases of AIDS, and approximately one-half of those who have contracted the disease have died.

Retroviruses were proposed as the causative agent of AIDS. Two such retroviruses now known to cause AIDS have been identified and isolated: LAV (lymphadenopathy-associated virus) and HTLV-III (human T-cell leukemia virus). It was later determined that LAV and HTLV-III are identical. Antibodies to these viruses are present in over 80% of patients diagnosed as having AIDS or pre-AIDS syndrome, and they have also been found with high frequency in the identified risk groups.

There is considerable difficulty in diagnosing the risk of development of AIDS. AIDS is known to develop in at least 10% of the individuals infected with HIV, although this percentage is suspected to be much higher.

A patient is generally diagnosed as having AIDS when a previously healthy adult with an intact immune system acquires impaired T-cell immunity. The impaired immunity usually appears over a period of eighteen months to three years. As a result of this impaired immunity, the patient become susceptible to opportunistic infections, various types of cancer such as Kaposi's sarcoma, and other disorders associated with reduced functioning of the immune system.

Another condition associated with HIV is AIDS-related complex, or ARC. This condition is thought to lead eventually to AIDS.

No treatment capable of preventing or reversing the immunodeficiency of AIDS or ARC is currently available. All patients with opportunistic infections and approximately half of all patients with Kaposi's sarcoma have died within two years of diagnosis. Attempts at reviving the immune systems in patients with AIDS have been unsuccessful.

Recently, it has been reported that 3'-azido-3'-deoxythymidine (AzT) is an antiviral agent that inhibits the infectivity and cytopathic effect of HIV in vitro. See Mitsuya, et al., Proc. Natl. Acad. Sci. USA 82, 7096-100 (1985). Preliminary results indicate that AzT exhibits toxicity in a clinical setting. See Yarchoan et al., Lancet 575-580 (1986). AzT was originally synthesized by Horwitz et al., J. Org. Chem. 29, 2076-2078, 1964. Its activity against Friend leukemia virus (a retrovirus) was reported as early as 1973 (see Ostertag et al., Proc. Natl. Acad. Sci. USA 71, 4980-4985 (1974) and Krieg et al., Exptl. Cell. Res. 116, 21-29, 1978 and references cited therein). The compounds of this invention are structurally quite similar to AzT, but are remarkably less toxic to normal cells and mice.

In general, inhibitors of cellular processes will often limit viral replication, but such agents are usually quite toxic for the host as well. Most of the antiviral drugs that have been discovered so far cannot be prescribed for a prolonged period of time because of their toxicity. For example, a compound structurally related to the compounds of the present invention, idoxuridine, is limited in clinical usefulness to topical application in ophthalmic solutions for treatment of herpetic keratitis because of its toxicity to normal cells. Clearly, there is a strong demand for new antiviral agents of low toxicity.

CS-87 and DDC are both known compounds. See, for example, Lin et al., J. Med. Chem. 26, 1691-1696 (1983), Lin and Mancini, J. Med. Chem. 26, 544-548, Colla et al., Eur. J. Med. Chem. - Chim. Ther. 295-301 (1985).

Lin et al tested the activity of both CS-87 and DDC against L1210 and sarcoma 180 cells in vitro and found that both of these compounds are inactive against both cell lines. Lin et al also reports that both CS-87 and DDC exhibit only marginal inhibitory activity towards two particular enzymes isolated from L1210 cells. Lin et al does not disclose a composition containing these compounds in a low concentration sufficient to inhibit replication of HIV or even that these compounds could be used to treat HIV.

Lin and Mancini reports that CS-87 and DDC are both inactive against L1210 cells. No other activity for these compounds is reported.

Colla et al reports that CS-87 is inactive against a variety of viruses. In particular, Colla et al reports that CS-87 is inactive against Coxsackie virus B4, polio virus-1, reovirus-1, parainfluenza virus-3, Sindbis virus and measles. Colla et al thus concludes that azido derivatives such as CS-87 do not have significant antiviral activity.

In light of the state of the art, it is clear that there remains a strong need for new antiviral agents, especially those with low toxicity to normal cells. More particularly, because of the high mortality of AIDS and the lack of an effective treatment for this disease, there remains a great need for development of new low toxicity agents for such treatment because AIDS patients require a long term therapy, possibly an entire life span. It was in this context that the present invention was achieved.

SUMMARY OF THE INVENTION

It is therefore an object of the present invention to provide new antiviral compositions having low toxicity towards uninfected cells.

It is a further object of this invention to provide compositions for inhibiting the growth of HIV.

It is yet another object of the present invention to provide a method for the prevention and treatment of infection by HIV.

These and other objects of the invention, which will hereinafter become more readily apparent, have been obtained by providing compositions having the following compound as an active ingredient:

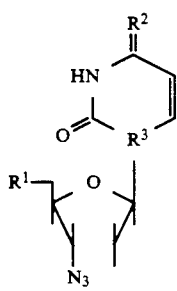

wherein $R^1$ may be OH, $NH_2$, phosphate, sulfate or a $C_{1-4}$ acyl group; $R^2$ may be O or NH; and $R^3$ may be C or N. Such compounds are provided as active ingredients in compositions and are contained therein in an amount sufficient to exhibit in vitro or in vivo activity against HIV. Further encompassed by the present invention is a method of prevention or treatment of AIDS or ARC, which involves administering a composition containing one or more of the above compounds to a person infected with HIV or at risk of acquiring the virus.

BRIEF DESCRIPTION OF THE DRAWINGS

A more complete appreciaton of the invention and many of the attendant advantages thereof will be readily obtained as the invention becomes better understood by reference to the following detailed description when considered in connection with the accompanying drawings, wherein.

DESCRIPTION OF THE PREFERRED EMBODIMENTS

The present invention is based on the discovery that 3'-azido-2',3'-dideoxyuridine (CS-87) and 3'-azido-2',3'-dideoxycytidine (DDC), C-nucleoside derivatives of these compounds, and, e.g., acylated and phosphorylated derivatives thereof exert antiviral activity against HIV while, at the same time, exhibiting remarkably low toxicity towards normal cells. Although CS-87 and DDC are known compounds per se, it has not hitherto been known that these compounds could exert potent antiviral activity against HIV, and, accordingly, compositions containing these compounds in the low concentrations sufficient to exert such activity against HIV have been unknown. Previously, various workers have reported that DDC and CS-87 have very little or no activity against both a wide variety of viruses and against certain tumor cells. Due to their low or nonexistent activity, relatively concentrated solutions of these compounds were utilized, but even these compositions did not result in significant activity. It has now been discovered that the 50% effective dose ($ED_{50}$) in cell culture of CS-87 against HIV is less than 1 micromolar, more precisely, 200 nanomolar. On the other hand, Colla et al have reported that CS-87 exhibits an $ED_{50}$ of 140 mg/ml (550 micromolar) against L1210 cell growth. With respect to viruses, CS-87 only exerted a marginal activity against HSV-1, exhibiting an $ED_{50}$ of 150 mg/ml (approximately 600 micromolar). Although CS-87 and related compounds exhibit reduced toxicity to normal cells (see Figures and Biological Data Section below), administration of a high concentration of such a drug would nevertheless produce some adverse side effects. By high concentration is meant a dosage which would result in a blood serum concentration of approximately 100 $\mu M$ or higher. Thus, compositions having a high concentration of the active ingredient are not considered to be therapeutically effective.

Although AzT is somewhat more active than CS-87 against HIV, it has a similar therapeutic index. The therapeutic index of a compound is determined by dividing the inhibitory or lethal dose for 50% of the population ($ID_{50}$ or $LD_{50}$) by the effective dose for 50% of the population ($ED_{50}$).

Figure 1:
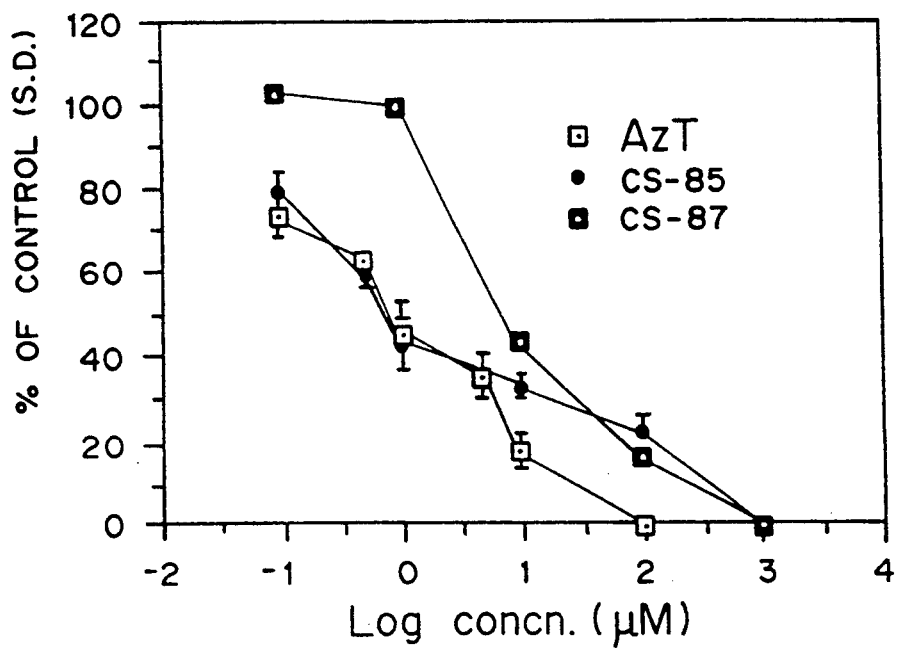
FIG. 1 is a graph showing the relative effects of AzT, CS-85 (3'-azido-2',3'-dideoxy-5-ethyl-uridine) and CS-87 on colony formation of human granulocytes-macrophage precursor cells.

The discovery that the present compounds are active against HIV at low concentrations and at the same time quite low in toxicity to normal host cells at the lower concentration was surprising, since a known compound of close structural similarity which is presently in clinical trials, AzT, exhibits a much greater toxicity as measured by various experiments. The results reported in FIG. 1 clearly show a significant difference in the effect of CS-87 on colony formation of human granulocytes-macrophage precursor cells in comparison to AzT. It should be noted that CS-87 appears to exert even lower toxicity towards these cells than CS-85, which is the subject of patent application U.S. Ser. No. 857,947, filed May 1, 1986 by the same inventors, now U.S. Pat. No. 4,681,933 which is hereby incorporated by reference herein.

As used in this invention, antiviral activity refers to the ability of a composition to inhibit the growth of HIV. The present compounds will also probably exhibit antiviral activity towards other retroviruses, such as murine retroviruses.

The ability of the present compositions to inhibit HIV may be measured by various experimental techniques. One such technique involves the inhibition of viral replication in human peripheral blood mononuclear cells. The amount of virus produced is determined by measuring the virus-coded reverse transcriptase (an enzyme found in retroviruses). Results with this assay are illustrated in Table 1 (see Biological Data section herein) and described further in the experimental examples below.

The compounds of this invention have the following structure:

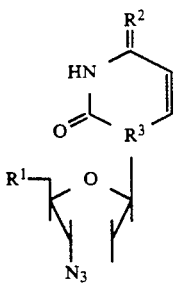

wherein $R^1$ may be OH, $NH_2$, $C_{1-4}$ acyl, sulfate or a phosphate group. $R^2$ may be O (cytidine derivatives), or NH (uridine derivatives). $R^3$ may be N or C.

The $C_{1-4}$ acyl group may be, for example, formyl, acetyl, propionyl, isopropionyl, etc. The compounds included in the present invention may also be in the form of salts such as, for example, potassium, sodium, and quaternary amine salts, etc. When amino groups are present on these compounds, they may be in the form of an acid addition salt such as the hydrochloride, acetate, hydrogen sulfate, etc.

Lyxo analogs of the present compounds are also encompassed within the scope of this invention. For example, the 3' substituent may have the opposite configuration from that shown in the figure.

A preferred group of compounds of this invention are those in which $R^2$ is oxygen and $R^3$ is nitrogen (a uridine derivative). A particularly preferred compound for a composition according to the present invention is CS-87, wherein $R^2$ is oxygen, $R^3$ is nitrogen, and $R^1$ is OH. Another preferred compound for a composition according to the present invention is DDC, wherein $R^2$ is NH, $R^3$ is N, and $R^1$ is OH.

It is to be understood that in addition the above compounds, further included in the scope of this invention are derivatives of the above-described compounds wherein 1 or more, preferably 1, hydrogen atom attached to a carbon atom is replaced by an ordinary organic substituent such as, for example, $C_{1-4}$ alkyl (straight chain or branched), halogen (especially Cl or Br), CN, OH, $NH_2$, NHR, $NR_2$ (wherein R is $C_{1-4}$ alkyl) etc. One specifically contemplated derivative is 5-methyl-3'-azido cytidine. This compound is a cytidine analogue of AzT and may be active on its own or may be converted in vivo by deamination (enzymatically or otherwise) to AzT. In the latter case, it would be acting as a pro-drug of AzT and would be expected to exhibit prolonged activity or reduced toxicity, or both, relative to AzT.

The compounds of this invention may be synthesized by methods known in the art. Lin et al, Colla et al, and Lin and Mancini, discussed above, each provide synthetic procedures which may be used to prepare these compounds. Each of the reactions reported therein may be readily optimized for the particular substituent pattern desired by one of skill in the art based on prior art references. The choice of solvents, temperatures, and other reaction conditions may be readily ascertained without undue experimentation. The yield of the desired product will depend to a large degree on the column chromatography technique used. A specific synthetic sequence leading to CS-87 (different from the above prior art methods) is illustrated hereinbelow.

Humans suffering from diseases caused by HIV can be treated by administering to the patient a pharmaceutically effective amount of one or more of the present compounds in the presence of a pharmaceutically acceptable carrier or diluent. A preferred carrier/diluent for oral administration is water, especially sterilized water. If administered intravenously, preferred carrier/diluents are physiological saline or phosphate buffered saline (PBS). The compounds according to the present invention are included in the pharmaceutically acceptable carrier or diluent in an amount sufficient to exert a therapeutically useful inhibitory effect on HIV in vivo without exhibiting adverse toxic effects on the patient treated. By "HIV inhibitory amount" is meant an amount of active ingredient sufficient to exert an HIV inhibitory effect as measured by, for example, an assay such as the one described herein in the Biological Data section.

There may also be included as part of the composition pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should produce a serum concentration of active ingredient of from about 0.2 to 40 μM. A preferred concentration range is from 0.2 to 20 μM and most preferably about 1 to 10 μM. However, the concentration of active ingredient in the drug composition itself will depend on bioavailability of the drug and other factors known to those of skill in the art.

It is to be noted that dosage values will also vary with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The tablets, pills, capsules troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Structurally related analogues such as phosphorylated and acylated derivatives of CS-87, and the uridine and C-nucleoside derivatives thereof will have similar activities at generally the same in vivo concentration ranges.

The invention now being generally described, the same will be better understood by reference to certain specific examples which are included herein for purposes of illustration only and are not intended to be limiting of the invention or any embodiment thereof, unless specified.

EXPERIMENTAL EXAMPLES

Synthesis of CS-87

5'-Trityl-2'-deoxyuridine (2)

A mixture of 2'-deoxyuridine (11.4 g, 0.05 mole) and trityl chloride (13.95 g, 0.05 mole) in dry pyridine 55 ml) was heated at 100° C. for 40 min. After cooling, the mixture was poured into an ice-water mixture (1 l), the precipitate filtered, washed with water, dissolved in chloroform, dried (MgSO$_4$), and then evaporated to a syrup (20.5 g, 85%).

3'-Mesyl-5'-trityl-2'-deoxyuridine (3)

The above syrup (20.5 g) (2) was dissolved in dry pyridine (50 ml) and methanesulfonyl chloride (10.0 g) was added dropwise and stirred for 3 hr. in an ice-water bath. Then, the mixture was poured into an ice-water mixture. The resulting precipitate was filtered, dissolved in chloroform, dried (MgSO$_4$), and then evaporated to a syrup (21.5 g, 81%).

2,3'-Anhydro-5'-trityl-2'-deoxyuridine (4)

To a refluxing ethanolic solution of 2 (21.5 g), 1N NaOH was added dropwise until no more starting material was present, as determined by tlc. The solvent was then evaporated to a syrup which was separated on a silica gel column using successive elution by chloroform, chloroform-methanol (50:1) and finally chloroform-methanol (20:1) to obtain a solid after evaporation of the solvents (11.3 g, 52%).

3'-Azido-5'-trityl-2',3'-dideoxyuridine (5)

A mixture of 4 (8.0 g, 16.7 mmole) and lithium azide (8.0 g, 163 mmole) in dimethylformamide (50 ml) was heated at 105°–110° C. for 20 hr. After heating, the solvent was evaporated to a syrup, which was thoroughly washed with water, and filtered to collect a white precipitate. The precipitate was purified on a silica gel column using chloroform-methanol (30/1) to yield 6.5 g (75%).

3'-Azido-2'3'-dideoxyuridine (6) (CS-87)

A mixture of 6 (4.7 g) and 80% acetic acid (30 ml) was heated at 95°–100° C. for 1 hr. After heating, the mixture was cooled in an ice-water mixture. The resulting white crystals (triphenylmethyl alcohol) were filtered off and the filtrate was evaporated. The resulting syrup was redissolved in methanol (10 ml) and the solution was stored in the refrigerator overnight. The resulting precipitate was filtered to collect crystals (390 mg). The above filtrate was evaporated to a syrup, triturated with ether and filtered to give another 1.1 g.

Biological Data

Antiviral Assay 1. 3–4 day-old PHA-stimulated human peripheral blood mononuclear cells from healthy volunteers ($1 \times 10^6$ cells per ml; volume=5 ml) are placed in a 25 cm$^2$ flask.

2. The medium, with ($2\times$ the final concentration) or without drug, is added to the flasks (5 ml; final volume=10 ml).

3. The flasks are then infected with about 5,000 cpm reverse transcriptase (RT)/ml or 50,000 cpm RT/flask and are then placed in a CO$_2$ incubator. LAV was obtained from the Centers for Disease Control, Atlanta. The RT levels of the stock virus is usually 0.8 to 1.3 million cpm RT/ml.

4. The next day (day 1), the supernatant is removed and the cells are replenished with fresh medium with or without drug ($1\times$ the final concentration). This step is optional.

5. On day 5, cells and supernatant are transferred to a 15 ml tube and centrifuged at about 900 rpm for 10 minutes. Four ml (or more if desired) of supernatant are removed. The virus is concentrated by centrifugation at 40,000 rpm for about 30 minutes. The resulting virus pellet is solubilized and the reverse transcriptase activity is then determined.

Using the RT assay, the results shown in Table 1 were obtained.

TABLE 1

EFFECT OF VARIOUS DRUGS ON THE REPLICATION OF
HIV IN HUMAN PERIPHERAL BLOOD MONONUCLEAR CELLS
(RT, P24 RIA AND WESTERN BLOT) - 10/24/86 expt
The amount of HIV p24 expressed in the supernatant obtained from
cells exposed to the drug is also shown in Table 1. Further, the
amount of viral protein, specifically p24 and p41, expressed
by the same cells was also determined by Western blot analysis.

| Treatment | Concn. μM | Mean DPM/Ml on day 5 3 day old cells | % Inhibition (corrected) | RIA p24 ng/ml | % Inhibition | Western Blot p24 | p41 |
|---|---|---|---|---|---|---|---|
| Control |  | 637,826 | 0.0 | 19.77 | 0.0 | 3+ | 2+ |
| CS-87 | 0.1 | 367,934 | 42.3 | 21.86 | 9.2 | 3+ | 2+ |

TABLE 1-continued

EFFECT OF VARIOUS DRUGS ON THE REPLICATION OF
HIV IN HUMAN PERIPHERAL BLOOD MONONUCLEAR CELLS
(RT, P24 RIA AND WESTERN BLOT) - 10/24/86 expt
The amount of HIV p24 expressed in the supernatant obtained from
cells exposed to the drug is also shown in Table 1. Further, the
amount of viral protein, specifically p24 and p41, expressed
by the same cells was also determined by Western blot analysis.

| Treatment | Concn. $\mu$M | Mean DPM/Ml on day 5 3 day old cells | % Inhibition (corrected) | RIA p24 ng/ml | % Inhibition | Western Blot p24 | p41 |
|---|---|---|---|---|---|---|---|
|  | 1 | 188,878 | 70.4 | 11.76 | 51.2 | 2+ | 1+ |
|  | 10 | 12,904 | 98.0 | 0.65 | 97.3 | 0 | 0 |
| AzT | 0.01 | 65,208 | 89.8 | 4.39 | 81.8 | 2+ | 1+ |
|  | 0.1 | 6,144 | 99.1 | 0.51 | 97.9 | 0 | 0 |
|  | 1 | 2,304 | 99.7 | 0.18 | 99.3 | 0 | 0 |
| No virus/no drug |  | 5,326 |  | 0.01 |  | 0 | 0 |
| Mean blank |  | 370 |  |  |  |  |  |
| Control for Rt |  | 336,432 |  |  |  |  |  |
| H9 marker |  |  |  |  |  | 4+ | 2+ |

Stock solutions prepared with 20 $\mu$l DMSO and about 10 ml medium

This experiment shows that CS-87 has significant activity in inhibiting replication of HIV in vitro.

Figure 2:
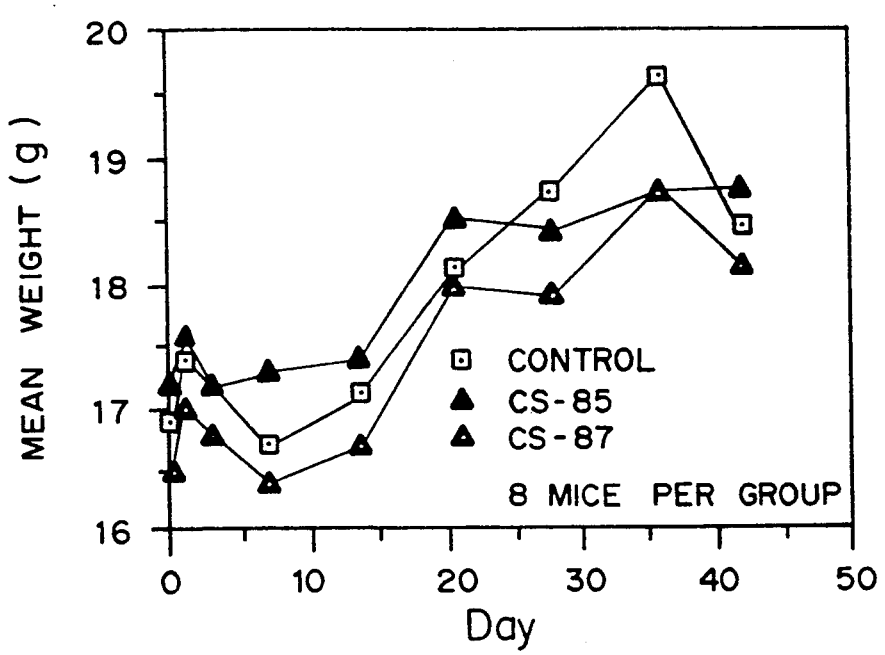
FIG. 2 is a graph showing the effect of CS-85 and CS-87 on the weight of BALB/c mice.
Figure 3A:
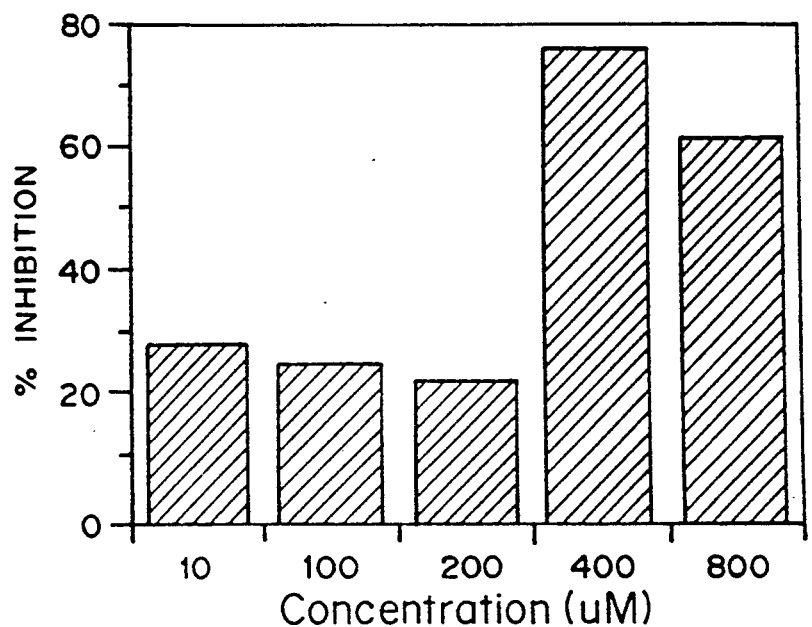
FIG. 3a shows the effect of CS-87 on the growth of Vero cells.
Figure 3B:
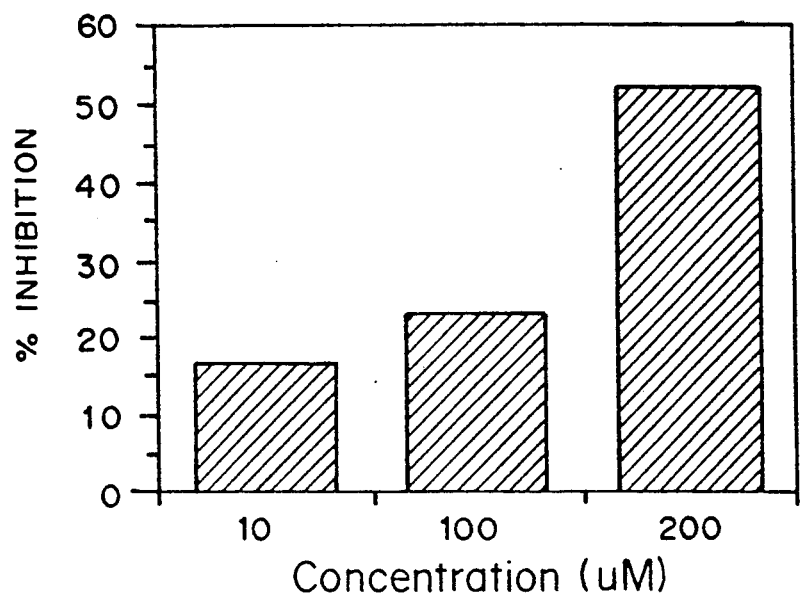
FIG. 3b shows the effect of CS-87 on the growth of human blood peripheral mononuclear (PBM) cells.

Various additional experiments were conducted to show the effects of CS-87 on the growth of certain cells, the effect on the weight of uninfected BALB/c mice, and the effect on liver enzymes in rhesus monkeys. Vero cells are very fast growing cells, and it can be seen from FIG. 3a that up to a concentration of about 400 micromolar, there is relatively little toxicity to these cells. The PBM cells are somewhat more sensitive to CS-87 than the Vero cells, but these cells will still tolerate a concentration of CS-87 of up to about 200 micromolar before significant inhibition is noted (see FIG. 3b). FIG. 2 shows the effect of CS-85 and CS-87 on the weight of uninfected BALB/c mice. It can be seen that there is no significant difference between CS-87, CS-85, and the control.

Figure 4A:
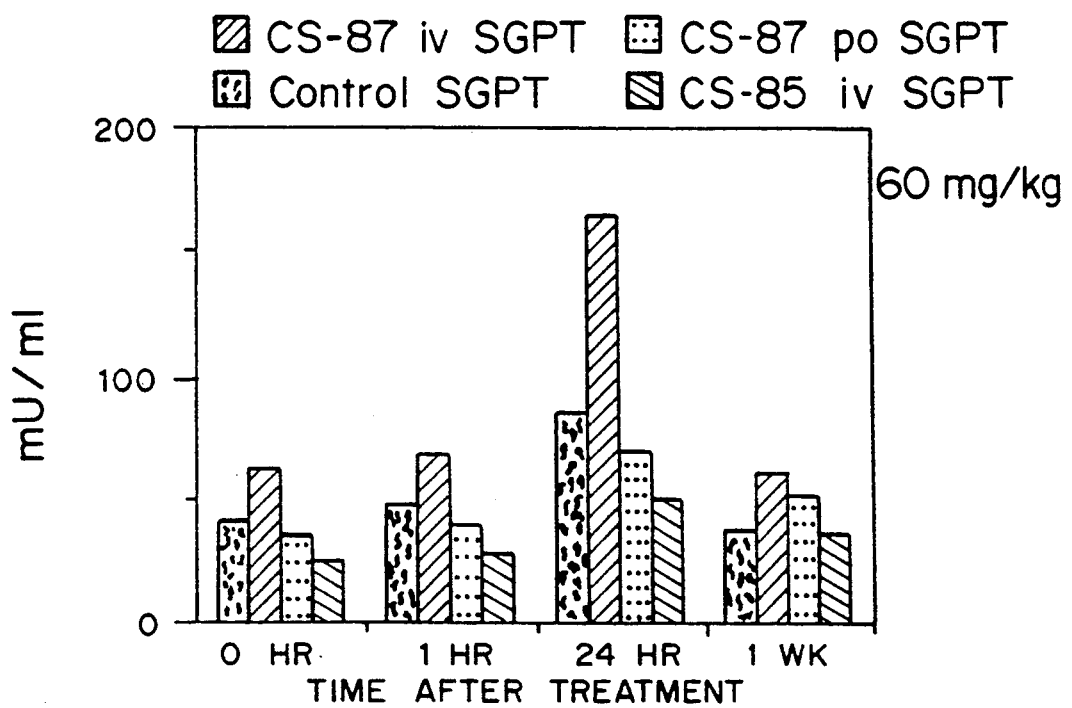
FIG. 4a shows the effects of CS-85 and CS-87 on liver enzyme SGPT in rhesus monkeys.
Figure 4B:
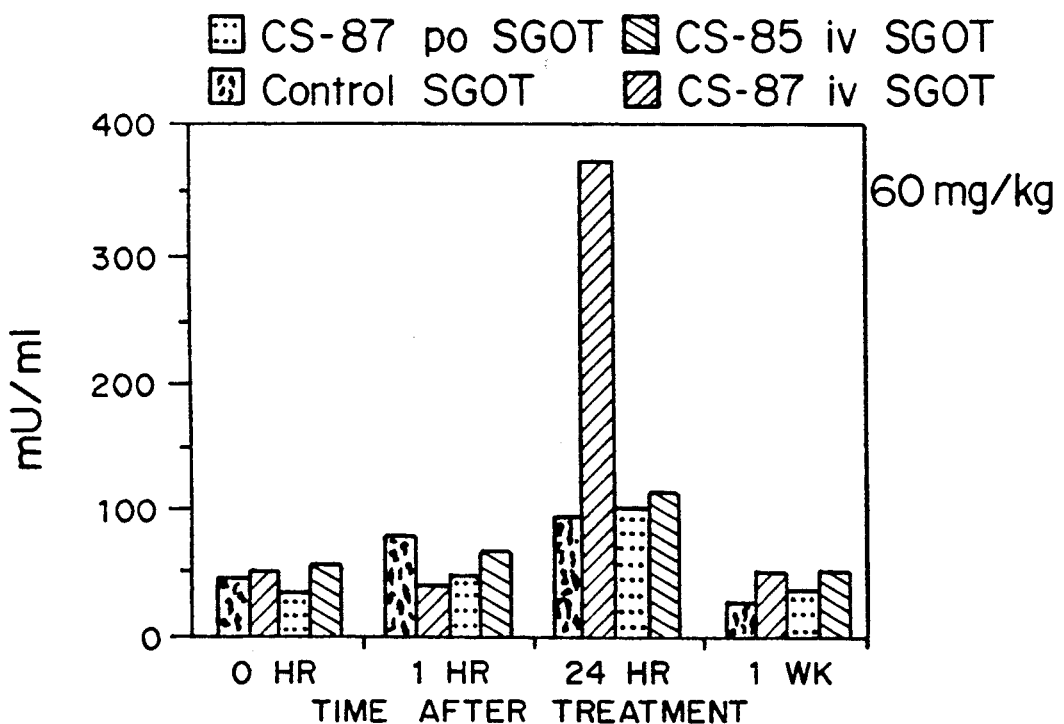
FIG. 4b shows the effects of CS-85 and CS-87 on liver enzyme SGOT in rhesus monkeys.
Figure 5:
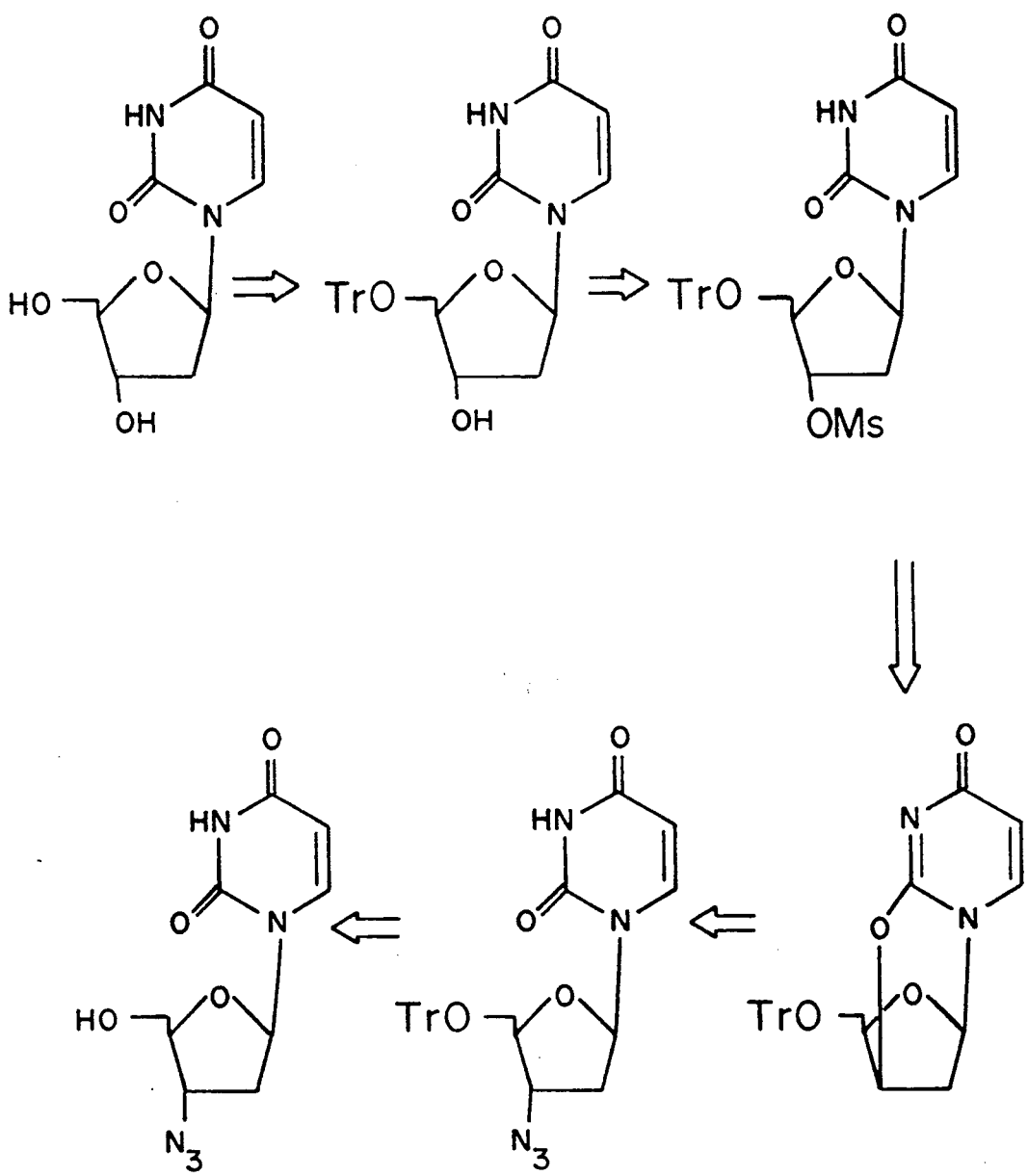
FIG. 5 shows a synthetic scheme for CS-87.

As can be seen in FIG. 4, there was a transient elevation in monkeys of SGPT and SGOT with intravenous administration of CS-87. However, the animals were back to normal after one week. It can be seen in FIG. 4 that oral administration (po) is less toxic than intravenous administration.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of inhibiting HIV comprising administering to a human infected with HIV an amount of a composition containing an active ingredient having the formula:

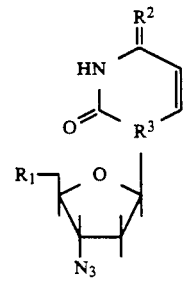

wherein $R_1$ is selected from the group consisting of $C_1$-$C_4$ acyl, sulfate, or amino, $R_2$ is O, and $R_3$ is N, or a pharmacologically acceptable acid addition salt thereof, in association with a pharmaceutical carrier in an amount inhibiting intracellular HIV replication.

2. The method according to claim 1, wherein the amount of said compound is sufficient to produce a human serum concentration of from 0.2 to 40 $\mu$M.

3. The method according to claim 2, wherein the amount of compound is sufficient to produce a human serum concentration of from 1 to 10 $\mu$M.

* * * * *